United States Patent
Zheng et al.

(10) Patent No.: US 11,696,907 B2
(45) Date of Patent: *Jul. 11, 2023

(54) WOUND HEALING COMPOSITION

(71) Applicant: WINERGEN TECHNOLOGIES INC., LTD., Shandong (CN)

(72) Inventors: Zhongli Zheng, Ipswich, MA (US); Wenyan Zhu, Shandong (CN)

(73) Assignee: WINERGEN TECHNOLOGIES INC., LTD., Shandong (CN)

( * ) Notice: Subject to any disclaimer, the term of this patent is extended or adjusted under 35 U.S.C. 154(b) by 193 days.

This patent is subject to a terminal disclaimer.

(21) Appl. No.: 17/177,361

(22) Filed: Feb. 17, 2021

(65) Prior Publication Data

US 2021/0236446 A1   Aug. 5, 2021

Related U.S. Application Data

(63) Continuation of application No. 16/343,428, filed as application No. PCT/CN2017/106873 on Oct. 19, 2017, now Pat. No. 10,980,762.

(30) Foreign Application Priority Data

Oct. 20, 2016   (CN) .......................... 201610914592.7

(51) Int. Cl.
| | |
|---|---|
| A61K 31/20 | (2006.01) |
| A61P 17/02 | (2006.01) |
| A61P 17/18 | (2006.01) |
| A61P 31/12 | (2006.01) |
| A61P 17/00 | (2006.01) |
| A61P 31/10 | (2006.01) |

(Continued)

(52) U.S. Cl.
CPC .............. *A61K 31/20* (2013.01); *A61K 8/361* (2013.01); *A61P 1/02* (2018.01); *A61P 1/04* (2018.01); *A61P 9/14* (2018.01); *A61P 17/00* (2018.01); *A61P 17/02* (2018.01); *A61P 17/18* (2018.01); *A61P 31/10* (2018.01); *A61P 31/12* (2018.01); *A61Q 17/04* (2013.01); *A61Q 19/00* (2013.01); *A61Q 19/06* (2013.01)

(58) Field of Classification Search
CPC .......... A61K 31/20; A61P 17/02; A61Q 19/00
See application file for complete search history.

(56) References Cited

U.S. PATENT DOCUMENTS

| | | | |
|---|---|---|---|
| 10,980,762 B2 * | 4/2021 | Zheng | ........................ A61P 1/04 |
| 2012/0276205 A1 | 11/2012 | Weissman et al. | |
| 2014/0287076 A1 | 9/2014 | Xing et al. | |

FOREIGN PATENT DOCUMENTS

| | | |
|---|---|---|
| CN | 104224924 A | 12/2014 |
| NL | 9101053 A2 | 1/1993 |
| WO | 03/032915 A2 | 4/2003 |

OTHER PUBLICATIONS

International Search Report and Written Opinion issued by the State Intellectual Property Office of China as the International Searching Authority for International Application No. PCT/CN2017/106873 dated Jan. 23, 2018.

(Continued)

*Primary Examiner* — Shengjun Wang
(74) *Attorney, Agent, or Firm* — Dechert LLP; Andrea L. C. Reid; Todd Macklin

(57) ABSTRACT

The present invention provides wound healing compounds, compositions thereof, and methods of treatment using the same.

19 Claims, 7 Drawing Sheets

Mechanical Injury Mouse Model

(51) Int. Cl.
    *A61P 1/04*     (2006.01)
    *A61P 1/02*     (2006.01)
    *A61P 9/14*     (2006.01)
    *A61Q 19/06*     (2006.01)
    *A61K 8/36*     (2006.01)
    *A61Q 17/04*     (2006.01)
    *A61Q 19/00*     (2006.01)

(56) References Cited

OTHER PUBLICATIONS

Raghallaigh et al., "The fatty acid profile of the skin surface lipid layer in papulopustular rosacea," British Journal of Dermatology. 2012; 166(2): 279-287.
Wikipedia WAX, 2020.
Wikipedia Jojoba oil 2020.

* cited by examiner

Figure 1: Mechanical Injury Mouse Model
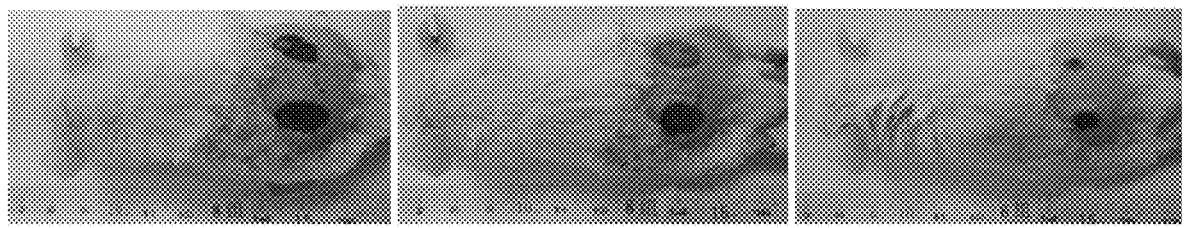

Figure 2: Mechanical Injury Mouse Model Comparative Study
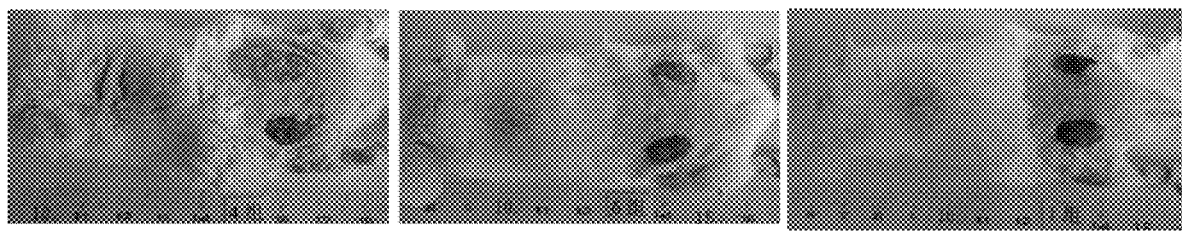

Figure 3: Hot Water Scalding Experiment
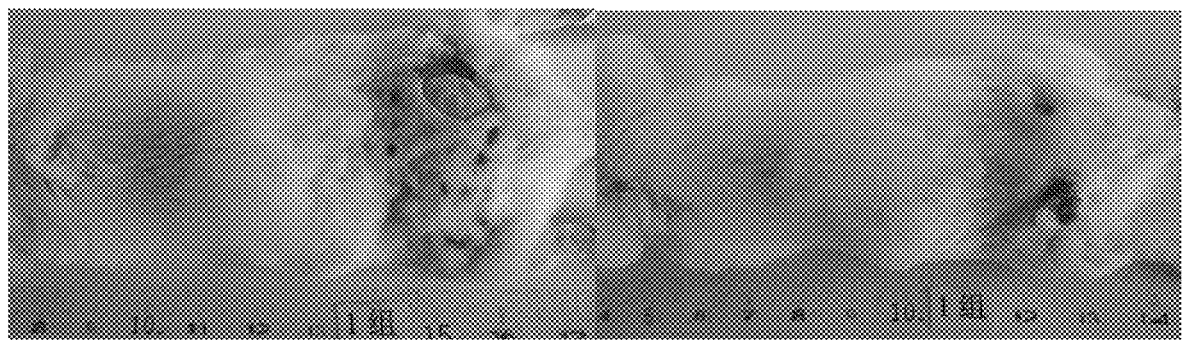

Figure 4: Mouse Burn Model
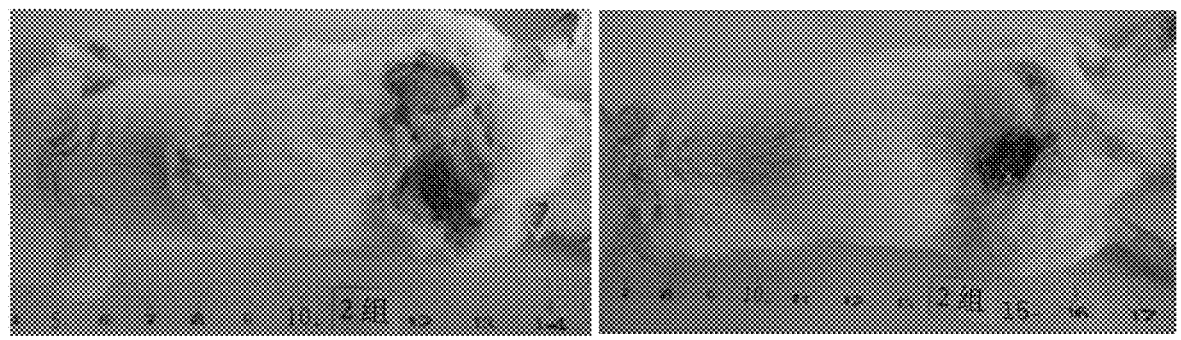

Figure 5: Diabetic Ulcer Patient

Figure 6: Non-Healing Diversion Wound
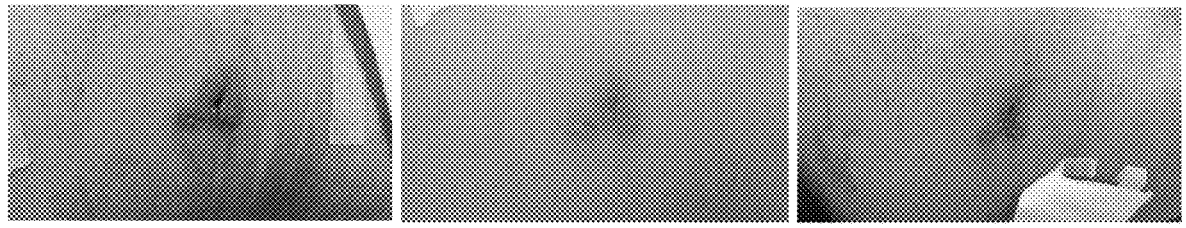

Figure 7: Lip Injury From Accidental Fall
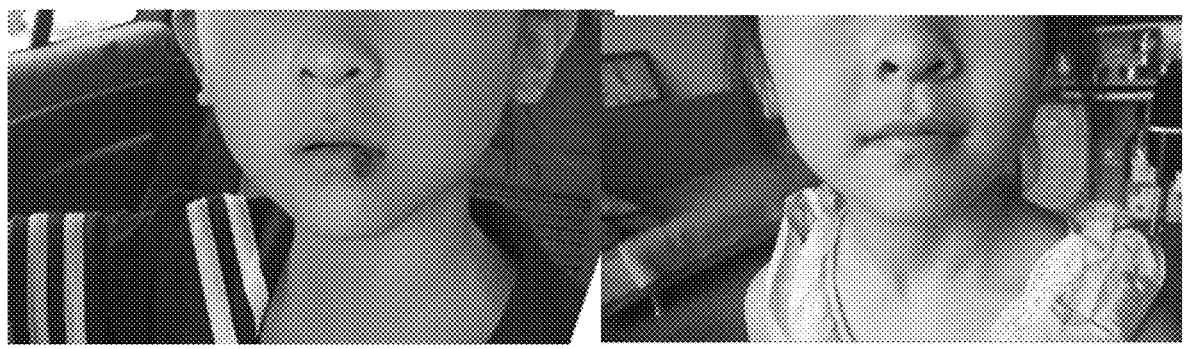
Figure 8: Non-healing pressure sores of a 80 year old women
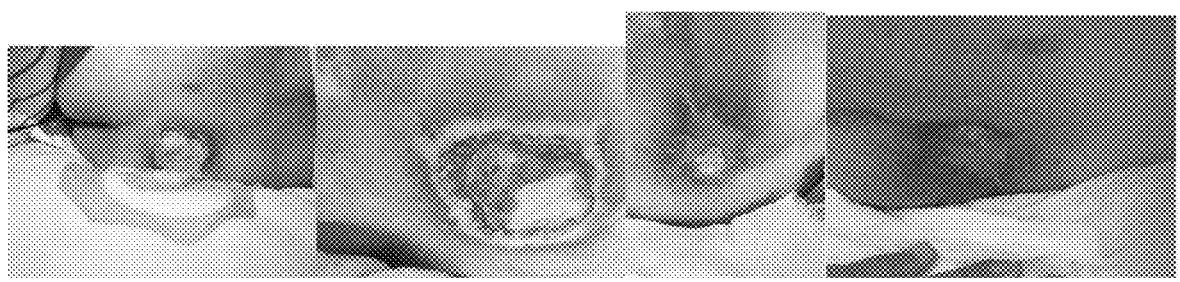

WOUND HEALING COMPOSITION

CROSS-REFERENCE TO RELATED APPLICATIONS

This application is a continuation of U.S. patent application Ser. No. 16/343,428, filed Apr. 19, 2019, which is a § 371 national stage of PCT International Application No. PCT/CN2017/106873, filed Oct. 19, 2017, claiming the benefit of Chinese Patent Application No. 201610914592.7, filed Oct. 20, 2016, the contents of each of which are hereby incorporated by reference in their entirety.

BACKGROUND OF THE INVENTION

Vegetable oils and butters are commonly used in cosmetic and pharmaceutical formulations as emollients, which are agents that moisturize the skin by promoting a reduction of transepidermal water loss (TEWL) (Leyden, J. J. & Rawlings, A. V. (2002) Skin Moisturization, Marcel Dekker, New York). However, there are very few scientific studies that show biological effects promoted by vegetable oils and butters when included in topical compositions. Due to varied fatty lipid compositions of the vegetable oils and butters used, beneficial effects of cosmetic and pharmaceutical formulations of vegetable oils on damaged skin tissue have been difficult to ascertain. There is still a need for better cosmetic and pharmaceutical compositions to repair skin damage caused by aging, diseases, surgical operation, burn/scalding and irradiation.

Currently preferred procedures for the treatment of chronic wounds, in particular venous ulcers, diabetic ulcers and pressure sores, include use of absorbent wound dressings. Current treatments also include use of simple medicated wound dressings, such as: INADINE™ (Registered Trade Mark of Johnson & Johnson), which is a slow release povidone iodine non-adherent dressing; FLAMAZINE™ (Registered Trade Mark of Smith & Nephew), which is a 1% silver sulphadiazine product for the treatment of infected wounds or ulcers; ASERBINE™ (Registered Trade Mark of Forley), which is a desloughing agent for ulcers and pressure sores; BETADINE™ (Registered Trade Mark of Seton), which is a povidone iodine ointment for decubitus and venous stasis ulcers; and VARIDASE™ (Registered Trade Mark of Lederle), which is a debriding agent containing streptokinase and streptodornase. Current or prospective treatments also include therapeutic pharmaceutical compositions, including: IAMIN® (Registered Trade Mark of ProCyte Corporation), which is a copper-peptide product; and PROCUREN® (Registered Trade Mark of Curative Technologies), which is a natural platelet-derived wound healing composition. However, a new treatment is still needed to heal the ulcers with the ability to regrow the skin and to reduce pain and itching.

A cutaneous burn can lead to partial or total destruction of the skin, of the soft tissues, of the ears and eyes, of the head hair and body hair, of the nails and even of the bones. Most burns affect only the skin, namely: the epidermis and the dermis. Most burn victims have severe pain associated with the burn injury. Severe burn patients also experience difficulty in skin regrowth, some need skin graft. Although pharmaceutical compositions intended for treating burns are already known. For example, Nederland patent number NL9101053 describes an oil-in-water emulsion forming a continuous film which is almost insoluble and impermeable, which is of use for treating irritated skin and healed burns; Sesame oil has been also used as a therapeutic aid to help the burn patients. However, a new treatment is needed to restore healing power of the burnt tissue with the ability to regrow the skin and to reduce pain.

United States Patent Application Publication US 2014/0287076 A1 (US national phase of PCT/CN2012/077432) by Junwu Xing et al., describes a fatty acid composition containing mainly linoleic acid, linolenic acid and oleic acid, as well as at least one selected from palmitic acid, palmitoleic acid, stearic acid, arachidic acid and docosanoic acid. It also discloses a natural extract from suaeda plants. Patent publication CN 104224924 A by Wang et al., similarly discloses compositions related to US 2014/0287076 A1, containing palmitic acid, stearic acid, oleic acid, linoleic acid, linolenic acid, behenic acid and plant oil. Both publications disclose complex mixtures as compositions. These publications did not make a distinction between free fatty acids (or fatty lipids) or esters. In addition, they report use of vegetable oils as components for the ointment, which may increase the uncertainty of the fatty acid composition and other plant derived products, making quality control of the compositions almost impossible to achieve as a pharmaceutical formulation. These and other shortcomings of these reported compositions have severe limitations as a useful pharmaceutical formulation.

SUMMARY OF THE INVENTION

It has been surprisingly found that only two free fatty acids, palmitic acid and behenic acid, are needed for effective treatment of a variety of wounds and skin damage. In contrast to the two reported patent publications using various mixtures of fatty acids, we also discovered that some of the unsaturated fatty acids in the Xing and Wang patent publications, such as linoleic acid and arachidonic acid, actually caused harmful inflammation to certain wounds, causing pain in some patients. The present invention also provides formulations using liquid wax as a carrier oil which is free from other fatty acid derivatives thus providing more practical formulations, compositions, and methods for treating wounds.

BRIEF DESCRIPTION OF THE DRAWINGS

FIG. 1 depicts the results of the mechanical injury mouse model as performed according to Example 1-a.

FIG. 2 depicts the results of the mechanical injury mouse model comparative study as performed according to Example 1-b.

FIG. 3 depicts the results of the hot water scalding experiment as performed according to Example 1-c.

FIG. 4 depicts the results of the mouse burn model as performed according to Example 38.

FIG. 5 depicts the results of administration of a therapeutic composition to a diabetic ulcer patient as described in Example 35.

FIG. 6 depicts the results of administration of a therapeutic composition to a non-healing wound as described in Example 35.

FIG. 7 depicts the results of administration of a therapeutic composition to a lip injury as described in Example 35.

FIG. 8 depicts the results of administration of a therapeutic composition to a non-healing pressure sore as described in Example 35.

DETAILED DESCRIPTION OF CERTAIN EMBODIMENTS

1. General Description of Certain Embodiments of the Invention

We have discovered, surprisingly, that only two free fatty acids, palmitic acid and behenic acid, effectively treat a variety of wounds and other forms of skin damage. In contrast to the two reported patent publications using various mixtures of fatty acids, we also discovered that certain of the unsaturated fatty acids in the Xing and Wang patent publications, such as linoleic acid and arachidonic acid, caused harmful inflammation to certain wounds, causing pain in some patients. In some embodiments, the present invention also provides formulations using liquid wax as a carrier oil which is free from other fatty acid derivatives thus providing more practical formulations, compositions, and methods for treating wounds.

As used herein, the term "therapeutic composition" refers to a composition comprising as active agent at least one of palmitic acid ($CH_3(CH_2)_{14}COOH$) and behenic acid ($CH_3(CH_2)_{20}COOH$). As used herein, the term "a provided therapeutic composition" refers to a composition comprising as active agent at least one of palmitic acid and behenic acid as described herein in various embodiments both singly and in combination. In some embodiments, the term "therapeutic composition" refers to a composition comprising as active agents both of palmitic acid ($CH_3(CH_2)_{14}COOH$) and behenic acid ($CH_3(CH_2)_{20}COOH$).

In some embodiments, the palmitic acid is in the form of a salt, prodrug, or ester. In some embodiments, the behenic acid is in the form of a salt, prodrug, or ester.

In some embodiments, the present invention provides a method for treating a dermatological condition or disorder in a patient in need thereof, wherein said method comprises administering to said patient a provided therapeutic composition, or formulation comprising a provided therapeutic composition.

In certain embodiments, the present invention provides a cosmetic and/or pharmaceutical formulation comprising a provided therapeutic composition, for treating tissue damage in a patient in need thereof. In some embodiments, a provided therapeutic composition is administered for treatment of skin tissue damage, pain and itch caused by aging, UV irradiation, burns and scalding. In some embodiments, the present invention provides therapeutic compositions administered for promoting healing of slow-healing wound tissue thus providing the ability of wounds to heal faster and with less scarring. In some embodiments, the present invention also provides applications and methods of treatment of slow healing tissue wounds due to old age or for wounds resulting from certain surgical procedures by administration of a provided therapeutic composition or formulation comprising a provided therapeutic composition. In some embodiments, the present invention also provides therapeutic compositions useful for the treatment and prophylaxis of chronic wounds such as venous ulcers, diabetic ulcers and pressure sores (decubitis ulcers). In some embodiments, the present invention also provides applications, formulations comprising a provided therapeutic composition and methods of treatment of skin disorders such as psoriasis, acne and eczema.

In some embodiments, the present invention provide a method of treating a necrotic skin condition in a patient in need thereof, comprising the step of administering to said patient a provided therapeutic composition, or formulation comprising a provided therapeutic composition.

In some embodiments, the present invention provide a method of treating a viral skin infection in a patient in need thereof, comprising the step of administering to said patient a provided therapeutic composition, or formulation comprising a provided therapeutic composition.

In some embodiments, the present invention provides for a therapeutic composition and a method of use thereof, for hair care.

In some embodiments, the present invention provides for a therapeutic composition and a method of use thereof, as an antimicrobial.

In some embodiments, the present invention provides a method of treating toenail fungus in a patient in need thereof, comprising the step of administering to said patient a provided therapeutic composition, or formulation comprising a provided therapeutic composition.

In some embodiments, the present invention provides a method of treating an ocular ulcer in a patient in need thereof, comprising the step of administering to said patient a provided therapeutic composition, or formulation comprising a provided therapeutic composition.

In some embodiments, the present invention provides a method of treating a mucosal ulceration in a patient in need thereof, comprising the step of administering to said patient a provided therapeutic composition, or formulation comprising a provided therapeutic composition.

In some embodiments, the present invention provides a method of treating a stomach ulcer in a patient in need thereof, comprising the step of administering to said patient a provided therapeutic composition, or formulation comprising a provided therapeutic composition.

In some embodiments, the present invention provides a method of treating a hemorrhoid in a patient in need thereof, comprising the step of administering to said patient a provided therapeutic composition, or formulation comprising a provided therapeutic composition.

In some embodiments, the present invention provides a method of treating a fistula associated with inflammatory bowel disease (IBD) in a patient in need thereof, comprising the step of administering to said patient a provided therapeutic composition, or formulation comprising a provided therapeutic composition.

In some embodiments, the present invention provides a method of treating scarring in a patient in need thereof, comprising the step of administering to said patient a provided therapeutic composition, or formulation comprising a provided therapeutic composition, in combination with laser irradiation.

In some embodiments, the present invention provides a method of treating dermis stretch marks or striae gravidarum in a patient in need thereof, comprising the step of administering to said patient a provided therapeutic composition, or formulation comprising a provided therapeutic composition, in combination with chemical pealing agents such as glycolic acid and or salicylic acid.

In some embodiments, the present invention provides a method of removing a tattoo in a patient in need thereof, comprising the step of administering to said patient a provided therapeutic composition, or formulation comprising a provided therapeutic composition, in combination with laser irradiation.

In some embodiments, the present invention provides a method of treating a wound or an infection of the skin in a patient in need thereof, comprising the step of administering to said patient a provided therapeutic composition, or formulation comprising a provided therapeutic composition, in combination with iodine.

In some embodiments, the present invention provides a method of treating burns or wounds in a patient in need thereof, comprising the step of administering to said patient a provided therapeutic composition, or formulation comprising a provided therapeutic composition. In certain embodiments, the present invention provides a method of treating nerve damage caused by a burn or wound in a patient in need thereof, comprising the step of administering to said patient a provided therapeutic composition, or formulation comprising a provided therapeutic composition. In some embodiments, the burn is caused by fire, electricity, (radioactive) radiation, ultraviolet radiation tissue damage, high temperature liquids, hot gases, high temperature solid, or chemically aggressive substances.

In some embodiments, the present invention provides a fatty acid composition and said at least one pharmaceutical formulations in the preparation of the repair tissue ulceration, or necrotic medicament.

In some embodiments, the present invention provides a method of treating psoriasis in a patient in need thereof, comprising the step of administering to said patient a provided therapeutic composition, or formulation comprising a provided therapeutic composition, in combination with variuos concetrations of linoleic acid, this combination provide itching relieve as well as repair the dermis damage caused by the psoriasis.

In some embodiments, the present invention provides a therapeutic composition, or formulation thereof, that is applied topically or externally.

In some embodiments, the present invention provides a therapeutic composition, or formulation thereof, and a method of use thereof for reducing itch, pain, and inflammation of skin and tissue. In some embodiments, a provided therapeutic composition, or formulation thereof, facilitates tissue regeneration of the lumen and mucosal tissue, muscle, and damaged nerve tissue. In some embodiments, the present invention provides a therapeutic composition, or formulation thereof, and a method of use thereof for providing repair functions; for providing a restorative treatment of a wound with faster healing, no infection, no scarring and no formation of characteristic purulent tissue. In some embodiments, the present invention provides a therapeutic composition, or formulation thereof, and a method of use thereof, for eliminating tissue exudate. In some embodiments, the present invention provides a therapeutic composition, or formulation thereof, and a method of use thereof, for eliminating inflammation and infection caused by trauma; promoting wound site healing of muscle, skin, mucous membranes, nerves and other tissues; and for treating and repairing a wound.

In some embodiments, the present invention provides a pharmaceutical preparation that can be made into various dosage forms suitable for external use, including: ointments, patches, suppositories, gauze agents, liniments, aerosol agents, powders and at least one film-forming agent, can be prepared in various dosage forms for topical use, solutions, powders, emulsions, and the like.

As used herein, the term "external wounds" refers to the outer flesh wound tissue of mechanical damage caused by a variety of forces, including, but not limited to cutting, punching jab, chopping, laceration, friction, tearing, impact, fall, fall caused by trauma.

As used herein, the term "internal injury" refers to injury suffered inside the body and includes fistulas, ulcers, and the like.

In some embodiments, the present invention provides a method of treating tissue ulceration or necrosis in a patient in need thereof, comprising the step of administering to said patient a provided therapeutic composition, or formulation comprising a provided therapeutic composition. According to the present invention, the tissue ulceration or necrosis include skin ulcers or necrosis, ulceration, or necrotic muscle, mucosal ulceration or necrosis and cavity ulceration or necrosis. For example, those ulcers caused by diabetes or varicose veins or ulceration caused by intractable ulcers, gangrene wounds, pressure ulcers, gastrointestinal ulcers and bleeding. Accordingly, in some embodiments, the present invention provides a method of treating a dermatological disorder in a diabetic patient in need thereof, comprising the step of administering to said patient a provided therapeutic composition, or formulation comprising a provided therapeutic composition, wherein the dermatological disorder is selected from intractable ulcers, gangrene wounds, pressure ulcers, gastrointestinal ulcers and bleeding.

In some embodiments, the present invention provides a method of repairing or treating a wound in a patient in need thereof, comprising the step of administering to said patient a provided therapeutic composition, or formulation comprising a provided therapeutic composition. According to the invention, the wound may include external body injuries and internal injuries. For example, surgical wounds, external injection, cannula or puncture, etc. caused by the surgical procedures including orthopedic surgery, cosmetic, gynecologic surgery and so on.

The present invention provides the above fatty acid composition and pharmaceutical preparations at least one application in the manufacture of cosmetics. Which refers to the cosmetic application, spraying or other similar methods, spread on the surface of any part of the body, such as skin, hair, finger nails, lips and teeth, so as to achieve cleaning, maintenance, beauty, modifications and changes in appearance or correction body odor, made into products including but not limited to cleaning cosmetics, hair cosmetics, basic cosmetics, cosmetics and cosmetic treatment and care.

It is believed that the provided therapeutic compositions and pharmaceutical formulations thereof can resist ultraviolet radiation damage to the human body. Accordingly, in some embodiments, a provided therapeutic composition is formulated into a sunscreen formulation for water sports such as sailing, swimming, diving and other professional personnel prevention and treatment of skin damage. In addition, a provided therapeutic composition and pharmaceutical formulations of the present invention also has the role of nourishing the skin, therefore, be used to prepare anti-chapped moisturizing agents and skin care preparations. In addition, it can be used to prepare the bath preparations, cosmetic preparations or care formulations.

Surprisingly, the present inventors have found that palmitic acid and behenic acid in any one alone also has some above treatment effect, but the effect is less significant. The combination of the two produce a synergistic effect.

For example, when applied in the form of ointment used, the paste evenly on the affected area, in general, the dosage should be based on the size of the wound, in order to be able to fully cover the wound even prevail. Injury to the wound surface area of 20-200 $cm^2$, for example, the amount of about 10-1000 mg/time, 1-3 times a day. When used in the form of an aerosol, the dosage of the active ingredient is preferably 0.1-100 mg/times, 1-3 times a day. In patch form, the content of active ingredient per pasted preferably 10-500 mg, daily exchange posted by 1-3. When used with other topical formulations, are also used in an amount of active ingredient is preferably 1-500 mg/times.

2. Formulation and Administration

Pharmaceutically Acceptable Formulations

According to another embodiment, the present invention provides a formulation comprising a provided therapeutic composition and a pharmaceutically acceptable carrier, adjuvant, or vehicle. The amount of a provided therapeutic composition in a formulation of this invention is such that is effective to treat a patient. In certain embodiments, the amount of a provided therapeutic composition in a formulation is such that is effective to treat a damaged tissue in a patient in need thereof, wherein the damaged tissue is caused by ulceration or necrosis. In some embodiments, the ulceration or necrosis is associated with diabetes. In some embodiments, the ulceration is a result of immobility.

In some embodiments, the present invention provides a formulation comprising: (a) a therapeutic composition; and (b) one or more carriers, adjuvants, or vehicles, wherein the therapeutic composition consists of palmitic acid and behenic acid. In some embodiments, the present invention provides a formulation comprising: (a) a therapeutic composition; and (b) one or more carriers, adjuvants, or vehicles, wherein the therapeutic composition consists of palmitic acid and behenic acid, and wherein the formulation is substantially free of other fatty acids.

The term "patient," as used herein, means an animal, preferably a mammal, and most preferably a human.

In some embodiments, the present invention provides a formulation comprising: (a) a therapeutic composition; and (b) one or more carriers, adjuvants, or vehicles, wherein the therapeutic composition consists of palmitic acid in an amount of about 1 to about 50% by weight of the formulation and behenic acid in an amount of about 0.5 to about 25% by weight of the formulation.

In some embodiments, the present invention provides a formulation comprising: (a) a therapeutic composition; and (b) one or more carriers, adjuvants, or vehicles, wherein the therapeutic composition consists of palmitic acid in an amount of about 2 to about 25% by weight of the formulation and behenic acid in an amount of about 0.5 to about 15% by weight of the formulation.

In some embodiments, the present invention provides a formulation comprising: (a) a therapeutic composition; and (b) one or more carriers, adjuvants, or vehicles, wherein the therapeutic composition consists of palmitic acid in an amount of about 5 to about 25% by weight of the formulation and behenic acid in an amount of about 0.5 to about 15% by weight of the formulation.

In some embodiments, the present invention provides a formulation comprising: (a) a therapeutic composition; and (b) one or more carriers, adjuvants, or vehicles, wherein the therapeutic composition consists of palmitic acid in an amount of about 2 to about 20% by weight of the formulation and behenic acid in an amount of about 0.5 to about 15% by weight of the formulation, wherein the total content of palmitic acid and behenic acid is less than 35% of the total weight of the formulation.

In some embodiments, the present invention provides a formulation comprising: (a) a therapeutic composition; and (b) one or more carriers, adjuvants, or vehicles, wherein the therapeutic composition consists of palmitic acid in an amount of about 3 to about 18% by weight of the formulation and behenic acid in an amount of about 0.5 to about 7% by weight of the formulation, wherein the total content of palmitic acid and behenic acid is less than 30% of the total weight of the formulation.

In some embodiments, the present invention provides a formulation comprising: (a) a therapeutic composition; and (b) one or more carriers, adjuvants, or vehicles, wherein the therapeutic composition consists of palmitic acid in an amount of about 6 to about 18% by weight of the formulation and behenic acid in an amount of about 1 to about 7% by weight of the formulation, wherein the total content of palmitic acid and behenic acid is about 5 to about 30% of the total weight of the formulation.

In some embodiments, a provided pharmaceutically acceptable formulation contains only palmitic acid and behenic acid as the active ingredient. In such embodiments, the content of the palmitic acid and behenic acid is about 1.5 to about 50% by weight of the formulation, the balance being pharmaceutically acceptable excipients.

In some embodiments, the present invention provides a method for preparing a provided formulation comprising the step of mixing the various components in accordance with the weight percentage ratios as defined above and herein. One of ordinary skill in the art will appreciate that various components of a formulation of the present invention (e.g., therapeutic compositions, carriers, vehicles, and adjuvants) are compounds known in the art, can be obtained in various ways, such as commercially available, it can also be synthesized, but also extracted from natural plant, microbes or animal materials.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In some embodiments, the present invention provides a formulation comprising a provided therapeutic composition and one or more pharmaceutically acceptable carriers, adjuvants, or vehicles known to one or ordinary skill in the art, selected from tartaric acid, malic acid, gum arabic, aspartame, carnauba wax, white petrolatum, white beeswax, β-cyclodextrin, propylene glycol, mooring poloxamer, gelatin or enteric flora and fauna plastic hollow capsules, soft capsules, acetic acid, sodium acetate, soy lecithin, cholesterol, egg yolk lecithin, starch, propyl paraben, methyl paraben, silicone oil, silica, titania, fumaric acid, citric acid, magnesium aluminum silicate, pectin, fructose, sodium alginate, black iron oxide, purple oxide, brown iron oxide, red iron oxide, yellow iron oxide, dextrin, sodium cyclamate, VASELINE®, xanthan gum, mixed fatty acid esters, cross-linked povidone, cross-linked sodium carboxymethyl cellulose, gelatin capsules, sodium metabisulfite, polysorbate 20, polysorbate 40, polysorbate 80, povidone K30, polyethylene glycol 400, polyethylene glycol 800, polyethylene glycol 1000, polyethylene glycol 1500, polyethylene glycol 4000, polyethylene glycol 6000, polyethylene alcohol, diethyl phthalate, potassium dihydrogen phosphate, dipotassium phosphate, disodium hydrogen phosphate, thimerosal, sulfate, calcium sulfate, maltodextrin, maltose, concentrated ammonia solution, propylparaben, oxybenzone ester, ethylparaben, hydroxypropyl-β-cyclodextrin, sodium hydroxide, light magnesium oxide, light liquid paraffin, agar, lactose, chlorobutanol, triethanolamine, sorbic acid, sorbitan single stearate (Span® 60), sorbitan monooleate (Span® 80), sorbitan monolaurate (Span® 20), sorbitan monopalmitate (Span® 40), sorbitan trioleyl esters (Span® 40), alkyl sulfates, alkenyl sulfates, sodium carboxymethyl starch, sodium carboxymethyl cellulose, stevia, anhydrous sodium sulfite, hydrochloric acid, dilute hydrochloric acid, lanolin, disodium edetate, cellulose acetate, ethyl acetate, isopropyl alcohol, stearic acid polyglycolic oxygen (40) esters, zein, various types of polysaccharides, polysaccharide, oligosaccharide and a variety of proteins, peptides ingredients, pregelatinized starch, sucrose stearate.

Therapeutic compositions, and formulations thereof, of the present invention may be administered topically. Therapeutic compositions, and formulations thereof, of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation or in a suitable enema formulation. Topical-transdermal patches are also contemplated.

For topical applications, therapeutic compositions, and formulations thereof, may be formulated in a suitable ointment containing a provided therapeutic composition suspended or dissolved in one or more carriers. Carriers for topical administration of a provided therapeutic compositions, and formulations thereof, include, mineral oil, liquid petrolatum, white petrolatum, propylene glycol, polyoxyethylene, polyoxypropylene compound, emulsifying wax and water. Alternatively, a provided therapeutic compositions, and formulations thereof, can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

In some embodiments, the present invention also provides a pharmaceutical formulation or a cosmetic formulation, comprising a provided therapeutic composition and at least one oily substance as the carrier oil for the formation of an ointment to be applied to the afflicted skin, wounds, or tissues. In some embodiments, a pharmaceutical formulation or a cosmetic formulation can also be an emulsion or a suspension in a suitable carrier system. In some embodiments, the total weight proportion of the active ingredients palmitic acid and behenic acid in a pharmaceutical formulation or a cosmetic formulation comprises between about 1.5 to about 40% by weight of the formulation. In some embodiments, a suitable carrier oil is selected from one or a combination of liquid substances comprising propylenediol, polyethylene glycol, liquid wax, glycerol trioleate, glycerol triarachidonate, jojoba oil, emu oil, pomegranate seed oil, sun flower seed oil, palm seed oil, olive oil and other plant seed oils which do not cause irritation to a mammal's skin tissue or wounds.

In some embodiments, the present invention also provides for a method of making a fatty acid composition, a pharmaceutical formulation, or a cosmetic formulation, comprising at least one fatty acid component, and a method of use thereof, for the treatment of an external wound or an internal injury.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of a provided therapeutic composition can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated.

Uses of Therapeutic Compositions and Pharmaceutically Acceptable Formulations

Therapeutic compositions, and formulations thereof, described herein are generally useful for wound healing and treatment of wounds. In some embodiments, the present invention provides a pharmaceutically acceptable formulation comprising a provided therapeutic composition and one or more pharmaceutically acceptable carriers, adjuvants, or vehicles. In some embodiments, the present invention provides a pharmaceutically acceptable formulation comprising a provided therapeutic composition wherein said formulation is for topical administration. In some embodiments, the present invention provides a pharmaceutically acceptable formulation comprising a provided therapeutic composition wherein said formulation is for topical administration to the skin.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

In addition to a provided therapeutic composition, a dosage form may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, a dosage form comprising a provided therapeutic composition can also include adjuvants such as wetting agents, emulsifying and suspending agents, and perfuming agents.

Compositions for rectal or vaginal administration are preferably suppositories which can be prepared by mixing a provided therapeutic composition with suitable non-irritating excipients or carriers such as cocoa butter, polyethylene glycol or a suppository wax which are solid at ambient temperature but liquid at body temperature and therefore melt in the rectum or vaginal cavity and release the provided therapeutic composition.

Dosage forms for topical or transdermal administration of a provided therapeutic composition include ointments, pastes, creams, lotions, gels, powders, solutions, sprays, inhalants or patches. In some embodiments, a provided therapeutic composition is admixed with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a provided therapeutic composition to the body. Such dosage forms can be made by dissolving or dispensing a provided therapeutic composition in the proper medium. Absorption enhancers can also be used to increase the flux of a provided therapeutic composition across the skin. The rate can be controlled by either providing a rate controlling membrane or by dispersing a provided therapeutic composition in a polymer matrix or gel.

In some embodiments, a provided therapeutic composition, or formulation thereof, is incorporated into one or more wound dressing agents (e.g., gauze, BandAid® dressings, cotton balls, cotton batting, cotton swabs, etc) for the treatment of a wound or skin disorder, as described herein, in a patient in need thereof.

In some embodiments, a provided therapeutic composition, or formulation thereof, is combined with one or more herbal medicines, chitosan powder, cuttlebone powder, and homeopathic agents known to one of skill in the art.

In some embodiments, a provided therapeutic composition, or formulation thereof, is provided in a bottle, jar, bag, or other container. Administration of a provided therapeutic composition, or formulation thereof, to a patient can be performed in any manner that results in application of the therapeutic composition, or formulation thereof, to the wound, infection, scar, skin disorder, etc, to be treated. Exemplary routes of administration include application with a finger, sponge, cotton swab, a brush, straw, or other tool to absorb and apply the therapeutic composition, or formulation thereof, to the affected area of the wound.

In some embodiments, a provided therapeutic composition is formulated into a cosmetic. One of ordinary skill in the art will appreciate that numerous suitable cosmetic formulations are amenable to comprise a provided therapeutic composition. Exemplary cosmetic formulations comprising a provided therapeutic composition include creams (e.g., moisturizers, anti-wrinkle creams, eye creams, etc), lipsticks (e.g., lip balm, lip gloss, etc), serums, lotions, foams, ointments, powders, and the like. Exemplary cosmetic formulations contemplated by the present invention also include makeup such as blusher, eye shadow, eye liner, mascara, and the like.

In some embodiments, the present invention provides an aerosol spray formulation comprising a provided therapeutic composition. Such aerosol spray formulations are especially suitable for administration to large wounds (i.e., those with a large surface area).

A provided therapeutic composition can be administered alone or in combination with one or more other therapeutic compounds, possible combination therapy taking the form of fixed combinations or the administration of a provided therapeutic composition and one or more other therapeutic compounds being staggered or given independently of one another, or the combined administration of fixed combinations and one or more other therapeutic compounds. In some embodiments, a provided therapeutic composition is administered in combination with one or more anti-aging agents, sunscreens, antioxidants, anti-wrinkle agents, and the like.

A provided therapeutic composition can besides or in addition be administered in combination with chemotherapy, radiotherapy, immunotherapy, phototherapy, laser therapy, surgical intervention, or a combination of these. Long-term therapy is equally possible as is adjuvant therapy in the context of other treatment strategies, as described above.

Those additional agents may be administered separately from a provided therapeutic composition, as part of a multiple dosage regimen. Alternatively, those agents may be part of a single dosage form, mixed together with a provided therapeutic composition in a single formulation. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a provided therapeutic composition may be administered with another therapeutic agent simultaneously or sequentially in separate unit dosage forms or together in a single unit dosage form. Accordingly, the present invention provides a single unit dosage form comprising a provided therapeutic composition, an additional therapeutic agent, and a pharmaceutically acceptable carrier, adjuvant, or vehicle.

The amount of both a provided therapeutic composition and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. In some embodiments, the amount of additional therapeutic agent in such compositions will be less than that required in a monotherapy utilizing only that therapeutic agent. In such compositions a dosage of between 0.01-1,000 μs/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

EXEMPLIFICATION

As depicted in the Examples below, in certain exemplary embodiments, compositions and methods of use thereof are described according to the following general procedures. It will be appreciated that, although the general methods depict the preparation and use of certain compositions of the present invention, the following general methods, and other methods known to one of ordinary skill in the art, can be applied to all compositions and subclasses and species of each of these compositions and methods of use, thereof as described herein. As used throughout the Examples, "liquid wax" refers to mineral oil.

Application Examples and Methods

Example 1-a: Mechanical Injury Mouse Model

Mouse strain: Kunming mice, male, approximately 35 g in weight, were used.

Wound induction: The back hair was removed using a 10% aqueous solution of sodium sulfide ($Na_2S$) to expose a 4×4 $cm^2$ section of hair-free skin. Under anesthesia using diethyl ether, two separate wounds symmetrical to the spine were created by cutting off the full-thickness of the skin layer to form two circular wounds, each 1.2 cm in diameter.

Experimental method: The left back side wound was used as a control without any treatment. The right side wound was treated immediately by evenly applying a layer of treatment Formulation FC every 12 hours for the full duration of the experiments. The experiments normally last for 7-14 days. Wound progression was observed and recorded continuously. Each data point obtained represents a group of 3 mice. (FIG. 1)

FIG. 1 from left to right: Left: Fresh wounds after the clotting phase [left wound (bottom): untreated; right wound (top): treated]; Center: 12 hours after the first application of Formulation FC; Right: 8 days after treatment. At 12 hours, a protective membrane is formed over the treated wound. After 8 days, there is a remarkable difference between treated and untreated wounds.

Example 1-b: Mechanical Injury Mouse Model Comparative Study

Comparative studies using the above mechanical wound model and treatment method as in Example 1-a above. As shown in FIG. 2, 12 hours after the first application of treatment, membrane formation is a good predictive indicator of wound healing effectiveness. The comparative products are two of the most popular OTC drugs for wound healing in China. (FIG. 2)

FIG. 2 from left to right: Left: Formulation FC; Middle: Mupirocin Ointment from Glaxo; Right: Yunnan Baiyao.

Example 1-c: Hot Water Scalding Experiment Protocol

Mouse strain: Kunming mice, male, approximately 30 g in weight, were used.

Wound induction: After anesthesia with diethyl ether, the back hair was removed using a 10% aqueous solution of sodium sulfide ($Na_2S$) to expose a 4×4 $cm^2$ section of hair-free skin. Pieces of square cotton gauze 1×1 $cm^2$, 3 mm thickness, were immersed in 100° C. boiling water, and then one hot gauze piece each was placed symmetrically on either side of the hairless areas of the mouse dorsal area. The hot gauze was removed after contacting the skin for 10 seconds, forming deep second degree scalding wounds. The left back (dorsal) wound was used as natural healing (untreated) control; the right dorsal wound was debrided to remove the damaged skin, and the ointment formulation-FC (Example 4 of Table 1) was applied every 12 hours for 15 days. Results were recorded and compared. Each group consisted of 4 mice. (FIG. 3)

FIG. 3 from left to right: The left picture is after 12 hours after the first treatment, the right side picture is on the $15^{th}$ day of treatment. The left picture shows a protective membrane is formed over the treated wound; after 15 days the difference is remarkable.

Examples 2-17, Treatment Formulation

Using liquid wax as a carrier to assess combinations of the active ingredients palmitic acid (PA) and behenic acid (BA) in the mouse model described in Example 1. Using the protocol outlined in Example 1, all animals were treated for 14 days. The representative formulations are summarized in Table 1 (Examples 2-17). The formulations described are selected to illustrate the principal, and are not meant to limit the scope of other possible formulations that are obtainable by those skilled in the art. In all the following tables and discussion: PA denotes palmitic acid; BA denotes behenic acid; PAT denotes tri-palmityl glyceride; and BAT denotes tri-behenyl glyceride.

Examples 18-34

Using the same ratio of PA to BA as in formulation FC in Example 4 of Table 1 as a representative composition to illustrate the scope of the carrier media or excipients. The same protocols as used in Examples 2-17 were used in Examples 18-34. The results are summarized in Table 2.

From these examples, it can be concluded that in addition to liquid wax and other synthetic molecules, oil lipids of plant or animal origin can be used as carrier media to form effective formulations for various applications, as long as these lipids are free from significant amount of free fatty acids. The active ingredients palmitic acids and behenic acid are most effective in their free acid forms or chemically equivalent forms in the skin environment.

Example 35, Clinical Applications (Table 3)

Formulation FC in Example 4 was used to ascertain clinical effectiveness in human subjects. Summary: 17 patients in our hospital from May 2013 to August 2014 have used this ointment. The patient population evaluated comprises: 10 cases of diabetic foot; dorsal ulcer in 5 cases; 3 cases of plantar ulcers; toe ulcer in 2 cases; 11 cases of defects in patients with soft tissue trauma; one burn case with tendon exposure; one case of lateral malleolus fracture with bone exposed; one case of non-healing soft tissue after a thigh abscess treatment; two cases of non-healing tissue after leg injury; 1 case of Achilles tendon rupture anastomosis wound healing; one case of toe hallux distal exostosis resection incision; four cases of wounds or skin grafting flap remaining after local wound is not closed.

Treatment methods: The patients were divided into two categories: those with deep soft tissue defects and those with superficial soft tissue defects. Deep defects are defined as the depth of the deep fascia deep ulcers, or with tendon or bone exposed. Superficial ulcers are defined as superficial fascia ulcers, with no tendon or bone exposed. All patients were treated by pre-debridement and VSD suction surgery until the wound was stable, with no infection or necrosis, then the wound cream formulation was applied once daily All patients first underwent debridement surgery to remove any necrotic tissue infection using a VSD suction device repeatedly with antibiotics treatment for 5-7 days, until wound granulation are covered with no new infection or necrosis. At this time, a layer of ointment about 1-2 mm in thickness was applied evenly to the wounds. The wounds were washed with saline solution before each use.

Treatment Results:

1. For the tendon or bone exposure wounds, this cream caused tissue growth and reduction of the exposure area.
2. For deep ulcers not associated with tendon or bone exposure, use of the ointment reduced the wound area. The early effect is obvious. After 2 weeks, some patients choose surgery to close the wounds, and others took home the ointment for self-application on their own.
3. For superficial wounds, all wounds were healed by the use of this ointment for 2 weeks.

Results for diabetic ulcer of the foot, treated with formulation FC, are shown in FIG. 5.

FIG. 5 from left to right: This patient's diabetic ulcer of the foot was at a serious stage, with all digits removed (the left two pictures) before treatment by Formulation-FC, after 15 days treatment, the ulcer is healed (right picture), sparing amputation of the entire foot.

Non-healing wound caused by diversion surgery: This patient's diversion tube opening remained unhealed after many months. At Day 17, the wound was totally closed, with a scab fully formed. After 1 month of treatment, the wound was totally healed. (FIG. 6)

FIG. 6 from left to right: This patient's diabetic ulcer of the foot was at a serious stage, with all digits removed (the left two pictures) before treatment by Formulation-FC, after 15 days treatment, the ulcer is healed (right picture), sparing amputation of the entire foot.

Lip injury caused by an accidental fall: This wound was completely healed without scar formation after 10 days of treatment. (FIG. 7)

FIG. 7 from left to right: The wound is completely healed without scar formation after 10 days of treatment.

Non-healing pressure sores of a 80 year old women: The non-healing sores was formed for over a year with 1.5 inch in diameter. It was treated by topical application twice a day with formula FC. The pictures bellow recorded the healing process: from left to right, day 0, day 4, day 30, day 45. At day zero, the wound was filed with pus, by day 4, the pus is greatly reduced, the tissue started new growth, by day 30, the wound was largely closed, by day 45, it was healed. (FIG. 8)

FIG. 8 from left to right: The non-healing sores was formed for over a year with 1.5 inch in diameter. It was treated by topical application twice a day with formula FC. The pictures bellow recorded the healing process: from left to right, day 0, day 4, day 30, day 45. At day zero, the wound was filed with pus, by day 4, the pus is greatly reduced, the tissue started new growth, by day 30, the wound was largely closed, by day 45, it was healed.

Example 36, Clinical Applications (Table 4)

With formulation FC in Example 4, using a similar protocol as in Example 35: Results (Table 4) show this formulation can repair various types of trauma to good effect over a wide range of applications, providing speedier healing, without scar tissue formation or purulent infection.

Example 37, Animal Model of Infected Wounds (Table 5)

Utilizing a group of 18 New Zealand white rabbits, the back hair was shaved and skin was cut, causing 4 cm long, 0.2 cm deep wounds. Wounds were swabbed with tap water smear, until the wounds swelled with purulent exudate.

Every three in one group (parallel experiments), were given topical treatment 2 times a day, each 100 mg. The healing time and treatment results as shown in Table 5.

Example 38, Animal Burn Wound Model, Rabbit (Table 6)

Utilizing a group of 18 rabbits, use alcohol swab to burn the back until the skin was charred.

Every three in one group (parallel experiments), were given drugs for treatment different from the above, 2 times a day, each 100 mg. The healing time and treatment results are summarized in Table 6.

Animal burn wound model, mouse (FIG. 4): Male, Kunming mice, ~30 g, were used. After anesthesia with diethyl ether, 10% solution of sodium sulfide is used to remove the hair on the back of the mice, forming a 4×4 $cm^2$ hairless area. A cotton ball 4 mm in diameter was soaked in anhydrous ethanol, and then ignited. One burning cotton ball was placed symmetrically on each side of the mouse dorsal hairless areas. After contacting the skin for 10 seconds, two deep second degree burn wounds were formed. The left back wound on the mouse was used as a natural healing control; the right wound was debrided to remove the damaged skin, and applied the ointment formulation-FC was applied every 12 hours for 15 days. Results were recorded and compared. Each group consisted of 4 mice. (FIG. 4)

FIG. 4 from left to right: The left picture is after 12 hours after the first treatment, the right side picture is on the $15^{th}$ day of treatment. The left picture shows a protective membrane is formed over the wound, after 15 days the difference is remarkable.

Example 39, Cosmetic Applications (Table 7)

PA and BA were added, as active ingredients, in the same ratio as in Example 4 of Table 1 to a standard cosmetic formulation using the following ingredients in Table-7 where the proportions of PA, BA and water used added up to 100%. The resulting emollient was evenly applied, 2 times daily, to human skin on the face, neck, hands, and around the eye regions where the skin was showing signs of aging, wrinkling and/or scaling. A similar skin area, on the opposite, symmetrical region, was used as a control. The results were observed and recorded for 1-7 days. Skin smoothness and tone were greatly improved at day 1, and by day 7 the improvement resulted in marked appearance of more youthful skin with reduced wrinkle and scaling.

Example 40, Cosmetic Applications

Using the same procedures and formulation as used in Example 39, except changing the PA and BA ratio to that used in Example 7 of Table 1, provided a marked improvement of skin youthfulness.

Example 41, Cosmetic Applications

Using the same procedures and formulation as used in Example 39, except changing the PA and BA ratio to that in Example 15, provided a marked improvement of skin youthfulness.

TABLE 1

(Examples 2-17)

| Example | Formulation Designation | Active Ingredients (in weight % of final formulation) | Excipients (or carrier solvent) | Positive therapeutic outcome evaluation | Notes |
|---|---|---|---|---|---|
| 2 | FA | PA, 1; BA, 0.5 | Liquid wax | Less fair | When total weight % of PA + BA is exceeding 30%, the formulation become too viscous and is difficult to apply to the wound surface, and may affect absorption by th skin tissue. PAT and BAT as control |
| 3 | FB | PA, 5; BA, 0.5 | Liquid wax | fair | |
| 4 | FC | PA, 12.5; BA, 4.5 | Liquid wax | great | |
| 5 | FD | PA, 25; BA, 0.5 | Liquid wax | good | |
| 6 | FE | PA, 1; BA, 1.5 | Liquid wax | Less fair | |
| 7 | FF | PA, 5; BA, 1.5 | Liquid wax | good | |
| 8 | FG | PA, 1; BA, 9 | Liquid wax | good | |
| 9 | FH | PA, 1; BA, 5 | Liquid wax | fair | |
| 10 | FI | PA, 12.5; BA, 9 | Liquid wax | good | |
| 11 | FG | PA, 25; BA, 4.5 | Liquid wax | Less fair | |
| 12 | FK | PA, 5; BA, 9 | Liquid wax | good | |
| 13 | FL | PA, 5; BA, 4.5 | Liquid wax | good | |
| 14 | FM | PA, 25; BA, 9 | Liquid wax | Less fair | |
| 15 | FN | PA, 9; BA, 12.5 | Liquid wax | good | |
| 16 | FO | PA, 5; BA, 12.5 | Liquid wax | fair | |
| 17 | FP | PAT, 12.5; BAT, 4.5 | Liquid wax | Not effective | |

TABLE 2

(Examples 18-34)

| Example | Excipient | Results evaluation | Notes |
|---|---|---|---|
| 18 (Example 4 of Table 1) | Liquid wax | great | |
| 19 | Pomegranate seed oil | great | |
| 20 | Sea buckthorn oil | great | |
| 21 | Olive oil | great | |
| 22 | Sun flower seed oil | great | |
| 23 | Emu oil | great | |
| 24 | Jojoba oil | great | |
| 25 | Isopropyl Myristate | poor | |
| 26 | Palmitoleic acid | poor | |
| 27 | Propylene diol | fair | Solubility low affects absorption |
| 28 | Poly ethylene glycol 400 | good | |
| 29 | Butylene diol | fair | Solubility low, affects absorption |
| 30 | Partially hydrolyzed olive oil | poor | Caused severe inflammation to wound area |
| 31 | Linoleic acid triglyceride | great | |
| 32 | Oleic acid triglyceride | great | |
| 33 | Linoleic acid | poor | Caused severe inflammation to wound area |
| 34 | Commercial arachidonic acid | poor | Caused severe inflammation to wound area |

TABLE 3

(Example 35)

| Classification | Non-healing wounds | Number of cases | Length of ointment use | Results |
|---|---|---|---|---|
| Diabetic ulcer (10) | Dorsal ulcer | 5 | 1-30 days | recovered |
| | Plantar ulcers | 3 | 1-30 days | recovered |
| | toe ulcers | 2 | 1-30 days | recovered |
| Traumatic ulcer (6) | Fracture postoperative infection | 1 | 7 days | recovered |
| | Abscess Drainage | 1 | 8 days | recovered |
| | Front shin bone ulcer | 2 | 1-15 days | recovered |
| | Achilles tendon rupture incision healing | 1 | 5 days | recovered |
| | Hallux warts phalanx resection | 1 | 8 days | recovered |
| Burn (1) | Back burns | 1 | 10 days | recovered |

TABLE 4

(Example 36)

| Wounds | Damage | Number of patients | Application length (days) | Results |
|---|---|---|---|---|
| Mechanical | Light to severe | 25 | 1-7 | recovered |
| Burn/scalding | Light to severe | 18 | 7-30 | recovered |
| Diabetic ulcers | Medium to severe | 6 | 10-60 | recovered |
| Pressure sore | Light to severe | 11 | 1-30 | recovered |
| Acne | Light to medium | 30 | 1-28 | recovered |
| UV/sun burn | severe | 4 | 1-3 | recovered |
| Other ulcers | Light to medium | 13 | 1-14 | recovered |

TABLE 5

(Example 37)

| Formulation used | Length of treatment, days | Results |
|---|---|---|
| Example 4 | 7 | Full recover, no significant scar |
| Example 15 | 7 | Full recover, no significant scar |
| Example 21 | 7 | Full recover, no significant scar |
| Example 23 | 7 | Full recover, no significant scar |
| Example 31 | 7 | Full recover, no significant scar |
| Example 32 | 7 | Full recover, no significant scar |

TABLE 6

(Example 38)

| Formulation used | Length of treatment, days | Results |
|---|---|---|
| Example 4 | 7 | Full recover, no significant scar |
| Example 7 | 7 | Full recover, no significant scar |
| Example 24 | 7 | Full recover, no significant scar |
| Example 27 | 7 | Full recover, no significant scar |
| Example 19 | 7 | Full recover, no significant scar |
| Example 20 | 7 | Full recover, no significant scar |

TABLE 7

(Example 39)

| | Other ingredients | CAS# | Weight (%) |
|---|---|---|---|
| Oil phase | SQUALANE | 111-01-3 | 0.5 |
| | SIMMONDSIA | — | 0.4 |

TABLE 7-continued (Example 39)

| | Other ingredients | CAS# | Weight (%) |
|---|---|---|---|
| | CHINENSIS (JOJOBA) SEED OIL | | |
| | CAPRYLIC/CAPRIC TRIGLYCERIDE | — | 0.2 |
| | DIMETHICONE | — | 0.5 |
| Water phase | GLYCERIN | 56-81-5 | 7 |
| | DIGLYCERIN | 59113-36-9; 25618-55-7 | 1 |
| | GLUCOSE | — | |
| | SODIUM HYALURONATE | 9067-32-7 | 0.2 |
| | SODIUM CHONDROITIN SULFATE | 9007-28-7; 9082-07-9 | 0.2 |
| | COLLAGEN AMINO ACIDS | — | 0.05 |
| | ARGININE | 74-79-3; 7200-25-1 | 0.2 |
| | FOLIC ACID | 59-30-3 | 0.4 |
| | POLYGLUTAMIC ACID | 25513-46-6 | |
| | BUTYLENE GLYCOL | 107-88-0 | |
| | BIS-PEG/PPG-16/16 PEG/PPG-16/16 DIMETHICONE | — | 0.3 |
| | CARBOMER | 9007-16-3; 9003-01-4; 9007-17-4; 76050-42-5; 9062-04-8 | 0.3 |
| additive | TRIETHANOLAMINE | 102-71-6 | 0.25 |
| | OCTANEDIOL | 629-41-4 | 0.1 |
| | PENTYLENE GLYCOL | 5343-92-0 | |
| | PHENOXYETHANOL | 122-99-6 | 0.5 |
| | CHLORPHENESIN | 104-29-0 | |

Example 42: Elimination of Stretch Marks

Mix 0.05%-70% glycolic acid or 0.05-20% salicylic acid to formulation FC to form a basic ointment. Applied this preparation daily to the affected areas by 5 people in each group, after 30 day treatment, all stretch mars have been removed.

Example 43: Relieve of Psoriatic Skin Disorder

Partially or wholly substituting liquid wax by 0.5-83% of linoleic acid to formulation FC to form a basic ointment. Applied this preparation daily to affected areas daily by 6 people, after 10 day treatment, the psoriatic scaring is eliminated, all patients reported itching relief 3 of the patients reported marked synergistic effect with Infliximab.

We claim:

1. A method for treating a burn or wound in a patient in need thereof, wherein said method comprises administering to said patient a formulation consisting of: (a) palmitic acid and behenic acid; and (b) mineral oil, wherein the palmitic acid is in an amount of about 6 to about 18% by weight of the formulation and the behenic acid is in an amount of about 1 to about 7% by weight of the formulation.

2. The method according to claim 1, wherein the burn or wound is caused by fire, electric power, radiation, ultraviolet radiation, a high temperature liquid, a hot gas, a hot solid, or a chemically aggressive substance.

3. The method according to claim 1, wherein the method comprises treating a wound.

4. The method according to claim 3, wherein the wound is caused by external damage or internal damage.

5. The method according to claim 3, wherein the wound is caused by mechanical damage or surgery.

6. The method according to claim 3, wherein the wound is caused by microbial infection.

7. The method according to claim 3, wherein the wound is difficult to heal due to old age or afflicting diseases.

8. The method according to claim 1, wherein the formulation is in a form of a cosmetic.

9. The method according to claim 8, wherein said cosmetic is selected from a sunscreen, an anti-chapped preparation, a skin preparation, a bath preparation, an eye cream, or a moisturizer.

10. The method of claim 1, wherein the formulation is in a form selected from an ointment, a patch, a suppository, a hard capsule, a soft capsule, an aerosol, a solution, an emulsion, a powder, a tablet, a pill, or an injectable.

11. A method for treating nerve damage caused by a burn or wound in a patient in need thereof, wherein said method comprises administering to said patient a formulation consisting of: (a) palmitic acid and behenic acid; and (b) mineral oil, wherein the palmitic acid is in an amount of about 6 to about 18% by weight of the formulation and the behenic acid is in an amount of about 1 to about 7% by weight of the formulation.

12. The method of claim 11, wherein the formulation is in a form selected from an ointment, a patch, a suppository, a hard capsule, a soft capsule, an aerosol, a solution, an emulsion, a powder, a tablet, a pill, or an injectable.

13. The method according to claim 11, wherein the method comprises treating a wound.

14. The method according to claim 13, wherein the wound is caused by external damage or internal damage.

15. The method according to claim 13, wherein the wound is caused by mechanical damage or surgery.

16. The method according to claim 13, wherein the wound is caused by microbial infection.

17. The method according to claim 13, wherein the wound is difficult to heal due to old age or afflicting diseases.

18. The method according to claim 11, wherein the formulation is in a form of a cosmetic.

19. The method according to claim 18, wherein said cosmetic is selected from a sunscreen, an anti-chapped preparation, a skin preparation, a bath preparation, an eye cream, or a moisturizer.

* * * * *